(12) United States Patent
Querner et al.

(10) Patent No.: US 8,916,491 B2
(45) Date of Patent: Dec. 23, 2014

(54) PROCESS FOR PRODUCING A METHANATION CATALYST AND A PROCESS FOR THE METHANATION OF SYNTHESIS GAS

(71) Applicants: Claudia Querner, Ludwigshafen (DE); Andrian Milanov, Mannheim (DE); Stephan Schunk, Heidelberg (DE); Andreas Strasser, Neckarsteinach (DE); Guido Wasserschaff, Neckargemuend (DE); Thomas Roussiere, Mannheim (DE)

(72) Inventors: Claudia Querner, Ludwigshafen (DE); Andrian Milanov, Mannheim (DE); Stephan Schunk, Heidelberg (DE); Andreas Strasser, Neckarsteinach (DE); Guido Wasserschaff, Neckargemuend (DE); Thomas Roussiere, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/670,815

(22) Filed: Nov. 7, 2012

(65) Prior Publication Data

US 2013/0116351 A1    May 9, 2013

Related U.S. Application Data

(60) Provisional application No. 61/556,848, filed on Nov. 8, 2011.

(51) Int. Cl.

| | | |
|---|---|---|
| *B01J 21/10* | (2006.01) | |
| *B01J 23/02* | (2006.01) | |
| *B01J 23/78* | (2006.01) | |
| *B01J 37/04* | (2006.01) | |
| *B01J 37/08* | (2006.01) | |
| *B01J 37/14* | (2006.01) | |
| *B01J 23/755* | (2006.01) | |
| *C10L 3/06* | (2006.01) | |
| *C10L 3/08* | (2006.01) | |
| *C07C 1/04* | (2006.01) | |
| *C07C 1/12* | (2006.01) | |
| *B01J 35/00* | (2006.01) | |
| *B01J 35/10* | (2006.01) | |
| *B01J 23/00* | (2006.01) | |
| *B01J 37/00* | (2006.01) | |
| *B01J 37/02* | (2006.01) | |
| *B01J 35/02* | (2006.01) | |
| *B01J 27/236* | (2006.01) | |

(52) U.S. Cl.
CPC ................ *B01J 21/10* (2013.01); *B01J 23/755* (2013.01); *B01J 35/002* (2013.01); *B01J*
(Continued)

(58) Field of Classification Search
None
See application file for complete search history.

(56) References Cited

U.S. PATENT DOCUMENTS

| | | | |
|---|---|---|---|
| 3,436,358 | A | 4/1969 | Thygesen |
| 3,865,753 | A | 2/1975 | Broecker et al. |

(Continued)

FOREIGN PATENT DOCUMENTS

| | | |
|---|---|---|
| DE | 26 24 396 A1 | 12/1976 |
| DE | 29 52 683 A1 | 7/1981 |

(Continued)

OTHER PUBLICATIONS

European Search Report issued Apr. 12, 2012 in Patent Application No. 11188238.7 with English Translation of Category of Cited Documents.

(Continued)

*Primary Examiner* — Melvin C Mayes
*Assistant Examiner* — Douglas Call
(74) *Attorney, Agent, or Firm* — Oblon, Spivak, McClelland, Maier & Neustadt, L.L.P.

(57) ABSTRACT

The present invention relates to a process for producing a catalyst for carrying out methanation reactions. The production of the catalyst is based on contacting of a hydrotalcite-comprising starting material with a fusible metal salt. The compounds brought into contact with one another are intimately mixed, thermally treated so that the metal salt fraction melts and subsequently subjected to a low-temperature calcination step and a high-temperature calcination step. The metal salt melt comprises at least one metal selected from the group consisting of K, La, Fe, Co, Ni, Cu and Ce, preferably Ni. The metal salt melt more preferably comprises/contains nickel nitrate hexahydrate. The hydrotalcite-comprising starting material is preferably hydrotalcite or a hydrotalcite-like compound as starting material, and the hydrotalcite-comprising starting material preferably comprises magnesium and aluminum as metal species.

The catalyst of the invention is preferably used for carrying out methanation reactions at elevated pressures (from 10 to 50 bar) and elevated temperatures.

14 Claims, 1 Drawing Sheet

(52) U.S. Cl.
CPC .... 35/1085 (2013.01); *B01J 35/023* (2013.01); *B01J 23/005* (2013.01); *C10L 3/08* (2013.01); *B01J 35/1014* (2013.01); *B01J 37/04* (2013.01); *B01J 35/006* (2013.01); *B01J 35/1061* (2013.01); *B01J 37/0009* (2013.01); *B01J 23/02* (2013.01); *B01J 37/08* (2013.01); *C10L 3/06* (2013.01); *B01J 35/109* (2013.01); *B01J 37/0201* (2013.01); *B01J 27/236* (2013.01); *B01J 35/1038* (2013.01); *B01J 35/0006* (2013.01); *C07C 1/12* (2013.01); *C07C 1/04* (2013.01); *B01J 37/0036* (2013.01); *B01J 23/78* (2013.01); *B01J 37/14* (2013.01)
USPC .......... 502/300; 502/328; 502/341; 518/715; 518/717

(56) References Cited

U.S. PATENT DOCUMENTS

| | | | |
|---|---|---|---|
| 3,866,353 A | | 2/1975 | Krumm et al. |
| 3,912,775 A | | 10/1975 | Broecker et al. |
| 3,988,262 A | | 10/1976 | Andersen et al. |
| 5,399,537 A | * | 3/1995 | Bhattacharyya et al. ....... 502/84 |
| 5,518,704 A | * | 5/1996 | Kelkar et al. .............. 423/420.2 |
| 5,767,040 A | * | 6/1998 | Bhattacharyya et al. ...... 502/327 |
| 6,071,433 A | * | 6/2000 | Bhattacharyya ............... 252/373 |
| 6,416,731 B1 | * | 7/2002 | Dohrup et al. ................. 423/653 |
| 2003/0005633 A1 | * | 1/2003 | Bhattacharyya et al. .... 48/198.1 |
| 2003/0172590 A1 | * | 9/2003 | Bhattacharyya et al. .... 48/198.7 |
| 2006/0270881 A1 | * | 11/2006 | Dakka et al. ................... 585/467 |
| 2008/0039313 A1 | * | 2/2008 | Jones et al. ...................... 502/68 |
| 2009/0261020 A1 | * | 10/2009 | Moon et al. ..................... 208/137 |
| 2010/0298133 A1 | * | 11/2010 | Takahashi et al. ............ 502/341 |
| 2011/0237689 A1 | * | 9/2011 | Bae et al. ....................... 518/702 |

FOREIGN PATENT DOCUMENTS

| | | | |
|---|---|---|---|
| DE | 195 03 522 A1 | 8/1996 | |
| EP | 0 031 472 A2 | 7/1981 | |
| EP | 2 226 308 A1 | 9/2010 | |
| EP | 2 308 594 A2 | 4/2011 | |
| KR | 10-0892033 B1 | 4/2009 | |
| WO | WO 2009/084208 | * 7/2009 | ................ C01F 7/00 |
| WO | WO 2009/115322 | * 9/2009 | ............. B01J 23/78 |
| WO | WO 2010/067945 | * 6/2010 | ............ C07C 29/153 |

OTHER PUBLICATIONS

F. Cavani et al., "Hydrotalcite-type Anionic Clays: Preparation, Properties and Applications", Catalysis Today, XP-002497610, Jan. 1, 1991, pp. 173-301.

U.S. Appl. No. 13/762,783, filed Feb. 8, 2013, Schunk, et al.

* cited by examiner

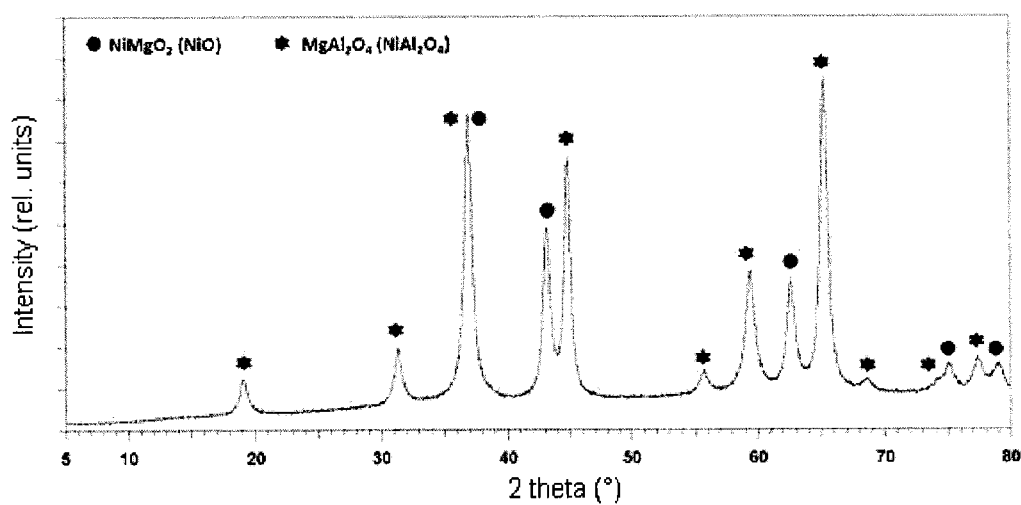

PROCESS FOR PRODUCING A METHANATION CATALYST AND A PROCESS FOR THE METHANATION OF SYNTHESIS GAS

The invention relates to a process for producing a methanation catalyst and a process for the methanation of CO—and/or $CO_2$-comprising gas streams, preferably at high temperatures. To produce the catalyst, hydrotalcite-comprising starting material is brought into contact with a fusible metal salt, preferably a salt comprising nickel nitrate, intimately mixed and subjected to a.) a thermal treatment step and b.) a calcination step.

The use of methanation for producing synthetic natural gas has been of great economic and industrial interest for half a century. The synthetic natural gas which can be produced by methanation is frequently referred to as substituted natural gas or SNG.

To present the prior art in the field of methanation, a brief review of the development of methanation processes and methanation catalysts will be given below.

Catalysts based on nickel-comprising active components have been used for methanation for many decades. In many of these catalysts, the nickel is present together with an oxidic support composed of aluminum oxide. The catalysts are often produced by precipitation of the active components in the presence of an aluminum-comprising support component or by coprecipitation of active component and support component. The products obtained in the precipitation are firstly dried and subsequently calcined. To obtain the catalyst in a suitable particle size, a shaping process is frequently inserted between drying and calcination.

Thus, for example, U.S. Pat. No. 3,912,775 describes the production of a precipitation product having the composition $Ni_6Al_2(OH)_{16}CO_3 \cdot 4H_2O$ which is obtained by precipitation of nickel nitrate and aluminum nitrate from aqueous solution by means of sodium carbonate solution. The precipitation can also be carried out in the presence of a support component. Furthermore, it is disclosed that the precipitation product is dried at a temperature in the range from 80 to 180° C. and calcined at a temperature in the range from 300 to 550° C. In the production process, the temperature increase between the drying process and the calcination process is effected using a temperature gradient by means of a controlled heating rate. To produce the methane-comprising product gas, naphtha and steam are used as starting materials and are brought into contact with the active composition at a temperature in the range from 270° C. to 460° C. and a pressure in the range 15.8-29.6 bar.

The efficiency of nickel-comprising catalysts for methanation can, according to U.S. Pat. No. 3,865,753, be increased by additionally adding magnesium species to the aluminum-comprising synthesis system. This synthesis and subsequent heat treatment gives a nickel-comprising magnesium aluminate as active composition which displays a high activity and stability in respect of methanation. As regards the precipitation product, it is advised that the divalent metals (magnesium and nickel) and the trivalent aluminum be present in a molar ratio of at least 1:1, with a preferred molar ratio of $M^{2+}$ to $M^{3+}$ being in the range from 2.5:1 to 3:1. The increased activity of the catalyst is also explained by, after drying, calcination and reduction, a magnesium spinel being formed during the reaction.

U.S. Pat. No. 3,988,262 discloses an improved catalyst which is obtained by the nickel-comprising component being deposited on the aluminum-comprising support in the presence of zirconium oxide. The catalyst according to the invention has a nickel oxide content of from 15 to 40% by weight, with a large part of the nickel oxide being reduced to nickel before commencement of the methanation.

According to DE 26 24 396, the thermal stability of the methanation catalysts can be increased by the catalyst having a certain proportion of molybdenum oxide. A molybdenum content of from 0.25 to 8% by weight of molybdenum or molybdenum oxide has been found to be advantageous.

EP 2 308 594 A2 discloses a nickel-comprising catalyst for producing synthesis gas from methane, water and carbon dioxide in a ratio in the range of 1.0/1.0-2.0/0.3-0.6. The improved stability of the catalyst is achieved by addition of Ce and/or Zr. In the experimental examples, a synthesis using magnesium-aluminum hydrotalcite as starting material is also disclosed. An impregnation process in which hydrotalcite as support is impregnated with an aqueous nickel nitrate solution, with the water subsequently being removed at 70° C. in a vacuum evaporator, is disclosed. In the process disclosed in EP 2 308 594 A2 for producing a synthesis gas, the feed stream used has a minimum content of 1 mol of water per mole of methane and the process is carried out at a pressure in the range from 0.5 to 20 atm. EP 2 308 594 A2 discloses an example in which the catalytic tests for producing synthesis gas were carried out at 10 atm.

EP 031 472 A2 discloses and claims a catalyst for methane production, which is produced using thermally decomposable salts of nickel, of cobalt and of magnesium which are fixed on a support. The support is converted by thermal treatment into the metal oxides.

DE 29 52 683 discloses a methanation catalyst which comprises Co and Ni species as active components. Aluminum oxides or mixed oxides of aluminum oxide and silicon dioxide or silicon dioxide are used as support materials, with the catalytic properties of the catalyst being improved by addition of magnesium-comprising salts to the synthesis mixture. In the context of the thermal treatment of the catalyst precursor material, the formation of a spinel-comprising phase is reported. The catalysts are used for methanation reactions which are carried out at temperatures below 500° C. and in which the pressure is in the region of atmospheric pressure.

One of the objects of the invention is to provide an improved process and an improved catalyst for the methanation of CO—and/or $CO_2$-comprising synthesis gas. In particular, a catalyst material whose thermal and mechanical stability is superior to that of the materials known from the prior art should be provided.

The formation of methane by reaction of carbon monoxide and/or carbon dioxide with hydrogen is a strongly exothermic process. In the presence of a suitable catalyst, the reaction normally proceeds to equilibrium. The catalytic formation of methane is carried out under adiabatic process conditions. The temperature increase within the reactor associated with the adiabatic process conditions is determined, inter alia, by the gas composition, the temperature of the gas fed in and the working pressure. The temperature increase when carrying out the methanation is typically in the range from 200 to 500° C.

The temperature of the gas fed into the reactor is selected so that the effectiveness of the catalyst with a high degree of conversion can be utilized. For this purpose, the gas fed in has to be preheated to a suitable inlet temperature. When carrying out the methanation process, it needs to be noted that the formation of methane within the catalyst bed is limited to a narrow reaction zone. The location of the reaction zone depends on the time for which the methanation process has been operated. At the beginning of the methanation process, methane formation initially extends to the region of the catalyst bed which is in the vicinity of the introduction of feed gas. With increasing time of operation and progressive deactivation of the catalyst within the reaction zone, this then moves in the direction of gas flow from the inlet region to the outlet region of the catalyst bed.

The inlet temperature and the process parameters should be selected so that the formation of $Ni(CO)_4$ is prevented. For example, in the methanation of CO-comprising feed gas by means of nickel-comprising catalysts, an inlet temperature of greater than 250° C. is required. The methanation of $CO_2$-comprising feed gas can also be carried out at lower inlet temperatures, e.g. at a temperature of 200° C. or even below 200° C. Methanation using feed gas which has a lower inlet temperature is also possible in conjunction with nickel-free catalysts.

Owing to the mode of operation mentioned here, the part of the catalyst bed which is located in the vicinity of the reactor outlet is subjected to higher thermal stress than the part of the catalyst bed which is located in the vicinity of the reactor inlet. The higher thermal stress on the catalyst material which is located in the catalyst bed in the vicinity of the reactor outlet occurs before this material is utilized for methanation. To limit the thermal stress on the catalyst, the temperature of the gas stream which leaves the reactor at the downstream end is monitored.

Correspondingly, the operating parameters when carrying out the methanation process are set so that the temperature of the product mixture at the reactor outlet does not exceed an upper temperature limit. This can be achieved, for example, by the feed stream being diluted with a certain proportion of product stream (recycle). The dilution reduces the CO and $CO_2$ content in the feed stream and the temperature increase caused by the exothermic reaction is limited.

It may be pointed out that all temperatures mentioned in the present disclosure in respect of the methanation process of the invention always relate to the temperature of the gas mixture obtained at the outlet end of the reaction space, unless indicated otherwise.

The objects mentioned here and also further objects which are not mentioned here are achieved by a process for producing a catalyst for the methanation of CO—and/or $CO_2$-comprising synthesis gases being provided. The process relates to impregnation of a starting material with a fusible metal salt, wherein the production process comprises the following steps:
(i) contacting of a fusible metal salt and finely divided hydrotalcite-comprising starting material,
(ii) intimate mixing of the fusible metal salt and the hydrotalcite-comprising starting material,
(iii) thermal treatment of the fusible metal salt and hydrotalcite-comprising starting material and heating of the mixture under conditions under which the metal salt is present in the form of a metal salt melt, preferably at a temperature in the range from 30 to 250° C., more preferably at a temperature in the range from 50 to 140° C.,
(iv) low-temperature calcination of the mixture at a temperature of <500° C., preferably at a temperature in the range from 250 to 500° C., with the duration of the low-temperature calcination preferably being in the range from 0.1 to 24 hours, preferably less than 2 hours, in the case of a continuous process preferably ≤1 hour,
(v) molding or shaping,
(vi) high-temperature calcination of the mixture at a temperature of ≥500° C., preferably at a temperature in the range from 500 to 1000° C., with the duration of the high-temperature calcination preferably being in the range from 0.1 to 24 hours, preferably less than 2 hours, in the case of a continuous process preferably ≤1 hour.

In a preferred embodiment, the calcination in process steps (iv) and (vi) is carried out using a defined heating rate and/or cooling rate, with the heating rate and/or cooling rate preferably being in the range from 0.01 to 10° C. per minute, more preferably in the range from 0.1 to 5° C. per minute.

In a preferred embodiment of the process, the shaping step (v) is followed by a sieving step.

Further preference is given to the metal salt fraction used in (i) comprising a nickel salt, preferably nickel nitrate hexahydrate.

The hydrotalcite-comprising starting material preferably has defined proportions of magnesium and aluminum, preferably at least 10 mol % of magnesium and at least 10 mol % of aluminum.

The invention also provides a catalyst for the methanation of CO—and/or $CO_2$-comprising synthesis gas, wherein this catalyst can be obtained by the following steps:
(i) contacting of a fusible metal salt and finely divided hydrotalcite-comprising starting material,
(ii) intimate mixing of the metal salt and the hydrotalcite-comprising starting material,
(iii) thermal treatment of the fusible metal salt and hydrotalcite-comprising starting material and heating of the mixture under conditions under which the metal salt is present in the form of a melt, preferably at a temperature in the range from 30 to 250° C., more preferably at a temperature in the range from 50 to 140° C.,
(iv) low-temperature calcination of the mixture at a temperature of <500° C., preferably at a temperature in the range from 250 to 500° C., with the duration of the low-temperature calcination preferably being in the range from 0.1 to 24 hours, preferably less than 2 hours, in the case of a continuous process preferably ≤1 hour,
(v) molding or shaping,
(vi) high-temperature calcination of the mixture obtained in the preceding steps at a temperature of ≥500° C., preferably at a temperature in the range from 500 to 1000° C., with the duration of the high-temperature calcination preferably being in the range from 0.1 to 24 hours, preferably less than 2 hours, in the case of a continuous process preferably ≤1 hour.

In the catalyst of the invention, the nickel is present in very highly disperse form on the support oxide and the support oxide consists of or comprises very small particles of $MgAl_2O_4$. This results in catalysts having an improved property profile which is reflected both in an improved sintering stability at high temperatures and in an improved carbonization behavior.

The production process of the invention has advantages over production processes based on precipitation methods. The process of the invention forms no significant amount of process water or the process of the invention can also be carried out in such a way that absolutely no process water is formed. At the same time as avoiding the formation of process water, precipitation reagents can also be saved. The problems associated with precipitation reagents, namely introduction of contamination, can be prevented.

As regards the synthesis of the catalysts of the invention, it may also be emphasized that an extremely energy-efficient and environmentally friendly process is provided because of the largely water-free production process.

Based on the total pore volume of the hydrotalcite-comprising support used, preferably hydrotalcite, the amount of water used is preferably ≤100%, more preferably ≤90%, even more preferably ≤70%, more preferably ≤50%, even more preferably ≤40%, particularly preferably ≤30% and more preferably ≤20%, of the total pore volume of the support. In a further preferred embodiment of the invention, the catalyst can be produced without addition of water since the water necessary for the synthesis is in this case supplied solely by the water of hydration of the salt.

In addition, a high metal loading or deposition of metal-containing phase on the support oxide or precipitation on a material which is a precursor of the support oxide can be achieved by means of the process of the invention.

The manner of mixing and the resulting combination of the hydrotalcite-comprising starting materials with the metal salt melt as per the process of the invention is extremely effective as regards the application and introduction of active components into the framework structure.

Without wishing to restrict the present invention by theoretical considerations, the following explanation of the formation of the catalyst of the invention appears plausible to us on the basis of structural studies on the formation mechanism: the treatment according to the invention of the hydrotalcite-comprising starting material with the nickel-comprising nitrate melt at a temperature of less than or equal to 500° C. leads to nanostructuring of the material. Magnesium is leached from the preformed layer-like carbonate-comprising precursor material. Together with the nickel, a nanocrystalline mixed crystal phase $Ni_xMg_{(1-x)}O$ having a periclase-bunsenite structure is formed from the hydrotalcite. In addition, an Mg spinel phase and aluminum oxide phases which are partly amorphous and are transformed into crystalline spinels in which the particles are nanocrystalline only at relatively high calcination temperatures are formed.

Catalysts which at temperatures up to 1000° C. have nickel crystallites which are smaller than 100 nm, preferably smaller than or equal to 70 nm and particularly preferably smaller than or equal to 40 nm, and have a high resistance to sintering and carbonization processes are obtained. The present nanostructuring of the material is particularly advantageous in respect of the catalytic properties thereof. In particular, the material according to the invention has been found to be an advantageous catalyst compared to the prior art which is also particularly suitable for the methanation of CO—and/or $CO_2$- comprising synthesis gases.

In a preferred embodiment of the invention, the catalyst support comprises a magnesium spinel which is in intimate contact with a mixed oxide phase of nickel and magnesium. In this catalyst or catalyst precursor according to the invention, both the nickel-comprising phase and the spinel-comprising phase have very small crystallite sizes. In the case of the spinel-comprising phase, the average crystallite size is <100 nm, preferably ≤70 nm, more preferably ≤40 nm.

In a further preferred embodiment of the invention, the phase composition of the catalyst of the invention is distinguished by the intensity of the diffraction reflection at 43.15°±0.15° 2θ (2 theta) (d=2.09±0.01 Å) being less than or equal to the intensity of the diffraction reflection at 44.83±0.20° 2θ (d=2.02±0.01 Å), with the intensity of the diffraction reflection at 43.15°±0.15° 2θ (2 theta) (d=2.09±0.01 Å) more preferably being less than the intensity of the reflection at 44.83±0.20° 2θ (d=2.02±0.01 Å) and the intensity ratio of the two diffraction reflections I(43.15°)/I(44.83°) even more preferably being in a range from 0.3 to 1.0, preferably from 0.5 to 0.99, more preferably from 0.6 to 0.97 and particularly preferably from 0.7 to 0.92. An illustrative depiction of a typical diffraction pattern (5-80° 2θ) of a catalyst according to the invention is shown in figure I.

The presence of small amounts of Ni spinel phase and possibly also NiO in the catalyst material of the invention or the catalyst precursor material is not ruled out. However, if an Ni spinel phase is present in the precursor material of the invention, it can be assumed that this will be transformed at the high pressures and the high temperatures of the use according to the invention of the catalysts.

The process of the invention enables all active metals which are present as metal salt melt in the temperature range from 30° C. to 250° C. and result in catalysts which display catalytic activity as methanation catalyst to be applied to hydrotalcite or to hydrotalcite-comprising starting material. In a preferred embodiment, promoters can be added to the metal salt melt and/or further support oxides, pore-forming agents or binders can be introduced into the synthesis system in addition to the hydrotalcite-comprising starting material.

To produce the catalyst of the invention, preference is given to using metal salts which do not decompose during melting or in the case of which the decomposition is greatly inhibited kinetically. Examples of such metal salts are, inter alia, nitrates, nitrites, halides, chlorates, bromates, iodates, sulfates, sulfites. Particular preference is given to nitrates, nitrites and salt melts comprising nitrates and nitrites. The addition of particular additives to the melts, for example urea, ethylene glycol, is encompassed.

The fusible metal salts can comprise, for example, Na, K, Ca, Mg, Sr, Ba, Al, La, Y, Mo, W, Nb, Zr, Ti, Fe, Co, Ni, Cu, a platinum metal and/or Ce as cationic species. Possible anionic species are, in particular, nitrogen-comprising anions such as nitrates and nitrites. However, other anions such as halogens, sulfates and sulfites and other inorganic and organic anions known to those skilled in the art can in principle be used. The metal salts preferably comprise at least one nickel-comprising or cobalt-comprising component, preferably nickel nitrate hydrate or cobalt nitrate hydrate, for example hexahydrate. Particular preference is given to nickel nitrate hexahydrate.

The term hydrotalcite-comprising starting material as used in the present disclosure means that the material used comprises at least one hydrotalcite-like compound as significant constituent and can optionally comprise oxidic additive and/or secondary constituents. The total proportion of the hydrotalcite-like compound and the oxidic additive is greater than 50% by weight, preferably greater than 70% by weight and particularly preferably greater than 90% by weight. In addition to hydrotalcite-like compounds and oxidic additives, the hydrotalcite-comprising starting material can also comprise secondary constituents which comprise, for example, metal salts and serve, for example, to adapt the metal concentration of trivalent to divalent metal salt. Such secondary metal salt constituents are present in amounts of less than or equal to 10% by weight, preferably less than or equal to 5% by weight.

Hydrotalcite-like compounds are mixed hydroxides of divalent and trivalent metals which are made up of polycations and have a layer structure. Hydrotalcite-like compounds are also referred to in the literature as anionic clays, layered double hydroxides (=LDHs), Feitknecht compounds or double layer structures. Divalent metals which can be used are, for example, metals from the group consisting of Mg, Zn, Cu, Ni, Co, Mn, Ca and Fe and trivalent metals which can be used are, for example, metals from the group consisting of Al, Fe, Co, Mn, La, Ce and Cr.

In a preferred embodiment, the hydrotalcite-like compound is composed of hydrotalcite. The hydrotalcites used for the process of the invention preferably comprise magnesium as divalent metal and aluminum as trivalent metal. The metals of the hydrotalcites used preferably comprise predominantly magnesium and aluminum.

The oxidic additive can also be a mixture, preferably a mixture comprising aluminum-comprising compounds. Examples of such aluminum-comprising oxidic additives are, inter alia, gibbsite, boehmite and pseudoboehmite. Typical contents of such aluminum oxides, hydroxides or oxide hydrates can be in the range from 30 to 95 percent by weight calculated on the basis of aluminum oxide. This corresponds to a molar proportion of aluminum based on total metal of from 26 to 84 mol %. Particular preference is given to the range from 50 to 80 percent by weight calculated on the basis of aluminum oxide. This corresponds to a molar proportion of aluminum based on total metal of from 44 to 70 mol %. Very particular preference is given to the range from 60 to 75 percent by weight calculated on the basis of aluminum oxide. This corresponds to a molar proportion of aluminum based on total metal of from 53 to 66 mol %.

The hydrotalcite-like compounds and the oxidic additive also display very intimate mixing. The same also applies to secondary constituents should these be comprised in the hydrotalcite-comprising starting material.

Such mixing can be effected, for example, by physical mixing of hydrotalcite-like and aluminum hydroxide-comprising powders. For example, powder mixing can be carried out in suitable industrial apparatuses such as mixers. Such mixing processes are known to those skilled in the art. A further possibility is to mix the hydrotalcite-like powder and the aluminum hydroxide-comprising powder in suitable dispersion media. As dispersion media, it is possible to use, for example, water, alcohols such as methanol, ethanol, propanol, butanol, ethylene glycol and/or butanediol and ketones such as acetone or methyl ethyl ketone. It is also possible for the dispersion media to be present as mixtures and comprise surface-active agents such as surfactants. Examples of such surfactants are, inter alia, polyethylene glycols, Mersolates, carboxylates, long-chain ammonium compounds such as CTAB.

Another possible way of achieving intimate mixing is the direct synthesis of a mixture of hydrotalcite-like and aluminum hydroxide-comprising substances by precipitation reactions. Such processes can be carried out, inter alia, as described in DE 195 03 522 A1 by hydrolysis of water-sensitive precursors, which allows many possible compositions. Other alternative processes for producing mixtures of hydrotalcite-comprising and aluminum hydroxide-comprising substances can be carried out on the basis of precipitation reactions from aqueous media. For example, it is possible to use carbonate-comprising precipitates or carbon dioxide-comprising gas mixtures can be allowed to act under pressure on suitable precursor solutions of metal salts or metal hydroxides.

Examples of hydrotalcite-comprising starting materials used for the purposes of the invention are products from Sasol which are marketed under the trade name Pural MG (Pural MG5 to Pural MG70 are commercially available, where Pural MG70 is an Mg—Al hydrotalcite without addition of aluminum hydroxide). Intimate mixing of magnesium- and aluminum-comprising hydrotalcites with other carbonates, hydroxides or hydroxycarbonates is also encompassed by the invention.

Preference is given to using hydrotalcites or hydrotalcite-like compounds having a particular purity for the process of the invention. The process for producing these hydrotalcite-like compounds which are particularly preferably used in the process of the invention is disclosed by J. P. van Berge et al. in DE 195 03 522 A1.

According to DE 195 03 522 A1, the hydrotalcites or hydrotalcite-like compounds are formed by hydrolysis of metal alkoxides by means of water and subsequent drying of the hydrolysis products obtained as precipitate. The metal alkoxides are formed by reaction of monovalent, divalent and/or trivalent alcohols with one or more divalent metals and/or one or more trivalent metals. The water used for the hydrolysis preferably comprises water-soluble anions selected from the group consisting of hydroxide anions, organic anions, in particular alkoxides, alkyl ether sulfates, aryl ether sulfates and glycol ether sulfates and inorganic anions, in particular carbonate, hydrogencarbonate, chloride, nitrate, sulfate and/or polyoxometalate anions. Ammonium is preferably used as counterion.

As hydrotalcite-comprising materials which are particularly suitable as starting materials for producing the catalyst and have been prepared by hydrolysis of metal alkoxides, mention may be made of materials which can be procured from Sasol under the trade names Pural MG5, Pural MG20, Pural MG30, Pural MG50 and Pural MG70. According to the information provided by the manufacturer, the numerical value in the product names is the percentage by weight of MgO present in the product. To obtain a total weight of 100%, the $Al_2O_3$ content has to be added to the proportion by weight of MgO. It should be noted that the figures here are based on the oxides, although the samples also comprise hydroxide groups and water. It is also possible in this case for the samples to be able to also comprise further anions, such as carbonate anions. It is also possible to procure materials which have other MgO to $Al_2O_3$ ratios. Particularly in those products or materials which have low magnesium contents, it is possible for these to comprise not only magnesium-aluminum-comprising hydrotalcite but also proportions of finely divided aluminum hydroxide or oxide hydrate.

A particularly preferred hydrotalcite-comprising starting material, viz. Pural MG30, comprises, for example, a mixture of hydrotalcite (i.e. a component having the composition $Mg_6Al_2(OH)_{18}*4H_2O$ or $Mg_6Al_2(OH)_{16}CO_3*4H_2O$) and boehmite, with the mixture having an overall $Al_2O_3/MgO$ ratio close to seventy to thirty % by weight. This number in the trade name of the product used here relates to the calcined material and means that in this particularly preferred example, the starting material has a boehmite content of about 55% by weight.

Instead of hydrotalcite, which is particularly preferred as constituent of the hydrotalcite-comprising starting material in the production process of the invention, it is also possible to use other metal hydroxides or hydroxycarbonates as starting materials. Particular preference is given to those which can be produced by the same synthesis process as hydrotalcites and hydrotalcite-like compounds.

It is also important for the purposes of the invention for the hydrotalcite-like starting material to have a preferred Al/Mg ratio. In a description of the composition of the hydrotalcite-like starting material in terms of the oxides comprised therein (in ignited form), the preferred alumina/magnesia ratio (i.e. the $Al_2O_3/MgO$ ratio) is in the range from 0.5 to 20 on a weight basis, with an alumina/magnesia ratio of from 1 to 10 on a weight basis being more preferred.

The preferred Al/Mg ratio is in the range from 1.5 to 2.5 on a molar basis, with an Al/Mg ratio of from 1.7 to 2.3 on a molar basis being more preferred. The preferred hydrotalcite-comprising starting material should be able to be converted preferably in significant proportions or particularly preferably virtually completely into a material having spinel or spinel-related structures or phase mixtures of such structures by high-temperature calcination at temperatures above 500° C.

Another important aspect of the invention is very intimate mixing of the hydrotalcite-comprising starting material with the fusible metal salt which gives close contact between the nickel species and the support precursor component and leads to unexpectedly good stabilization of the nickel species. After calcination, this leads, as mentioned above, to a mixed oxide phase having the composition $Ni_xMg_{(1-x)}O$ where x=0.3-0.7, preferably 0.4-0.6. (The content range of x=0.3-0.7 corresponds to an NiO content of about 44-81% by weight and in the case of x=0.4-0.6 the NiO content is about 55-73.5% by weight.) Furthermore, a certain proportion of Ni spinel could be detected by means of XRD analyses after calcination.

The XRD results indicate that depletion of Mg species occurs in the mixed oxide phase $Ni_xMg_{(1-x)}O$. The Mg species replace Ni species in the Ni spinel. A possible explanation, which does not constitute a restriction of the invention, would be that a proportion of the aluminum continues to be present as aluminum oxide hydrate even at high temperatures. Under reductive conditions at high temperatures, elimination of metallic nickel from the mixed oxide phase $Ni_xMg_{(1-x)}O$ could occur, with the magnesium liberated then reacting with the aluminum oxide hydrate to form magnesium-aluminum spinel.

As regards the molar ratio of metal species in the hydrotalcite-comprising starting material $M_{HT}$ and metal species in the salt melt $M_S$, it can be stated that the molar ratio of metals $M_{HT}/M_S$ is always greater than 1. The molar ratio $M_{HT}/M_S$ is preferably in the range from 15 to 1.5 and more preferably in the range from 10 to 3. The use of a preferred ratio is important to ensure the conditions for good mixing of the components and homogeneous coating of the hydrotalcite and thus ensure the nanostructuring, in particular the high dispersion and finely divided nature of the nickel and of the mixed oxide composed of Ni and Mg and the finely divided nature of the Mg spinel, of the material according to the invention.

In a preferred embodiment, the pulverulent hydrotalcite-comprising material is heated before contacting with the fusible metal salt and on being brought into contact with the metal salt has a temperature in the range from 30 to 250° C., preferably in the range from 50° C. to 140° C.

The temperature required for melting the metal salt depends on the properties of the metal salt or metal salt mixture used in each case. Metal salts which are particularly suitable for the process of the invention have a melting point in the range from 30 to 250° C.

In one of the preferred embodiments of the process of the invention, the hydrotalcite-comprising starting material is brought into contact with the metal salt melt. To suppress solidification of the metal salt melt during contacting and mixing with the hydrotalcite, it is advantageous to preheat the metal salts to a temperature which is at least 10° C. above, preferably 20° C. above, the temperature of the melting point of the salts or salt mixture used in each case.

In selecting the process parameters for contacting of the powder with the melt, it has to be taken into account that the water of crystallization of the hydrotalcite and of the metal salt melt is subjected to evaporation. This evaporation depends on the temperature, the gas exchange, the gas atmosphere and the duration of the process. Complete evaporation of the water of crystallization can be undesirable since decomposition of the salt or of the hydrotalcite can then occur before homogenization of the mixture. Solidification of a region in the melt which has not yet been intimately mixed with the hydrotalcite-comprising material adversely affects the homogeneity of the distribution of the metal species on the solid hydrotalcite-comprising starting material.

The duration of contacting should be very short, i.e. preferably less than or equal to 30 minutes.

The gas atmosphere should preferably comprise a certain proportion of water in order to suppress the decomposition of metal salt or the hydrotalcite-comprising starting material during mixing. The content of water vapor here can be, for example, in the range from 0 to 10% by volume.

It is advantageous to heat the hydrotalcite-comprising starting material to a temperature which corresponds approximately to the temperature of the salt melt before bringing it into contact with the salt melt in order to avoid uncontrolled solidification of the salt melt.

I. Contacting and Mixing of Hydrotalcite with Metal Salt

It firstly has to be pointed out that the process step of contacting of the hydrotalcite-comprising starting material with the metal salt is not subject to any limitation. However, a number of embodiments of contacting which are advantageous are indicated below.

For example, the hydrotalcite-comprising starting material can firstly be combined and mixed with the pulverulent metal salt at a temperature below the melting point of the salt before the latter is melted. The substances are firstly combined cold. The combining and mixing can be carried out in a plurality of steps or in a single step.

In another preferred embodiment of the process of the invention, the pulverulent hydrotalcite-comprising starting material is placed in a vessel and the metal salt melt is added thereto while agitating the solid. The melt can be added to the hydrotalcite a little at a time in a plurality of steps or in a single step.

In still another embodiment, which is likewise preferred, the hydrotalcite-comprising starting material is first coated with the metal salt before the latter is then melted. Here, it is possible, for example, firstly to suspend the hydrotalcite-comprising starting material in water and combine it with a metal salt solution. The mixture of the hydrotalcite-comprising starting material and the metal salt solution forms a suspension which can, for example, be dried by spray drying.

To ensure intimate mixing of the fusible metal salt and the hydrotalcite-comprising starting material, the components which have been brought into contact with one another have to be mixed and homogenized by means of mechanical mixing elements. As mixers, it is possible to use, for example, powder mixers, tumblers, kneaders, etc. The suitable industrial means for mixing should be known to a person skilled in the art. The duration of the mixing step is preferably ≥2 minutes, more preferably ≥10 minutes and even more preferably ≥30 minutes.

The mixing as per step (ii) and the thermal treatment as per step (iii) are preferably carried out simultaneously. The material to be mixed is preferably heated during the mixing process in order to prevent solidification or crystallization of the salt melt.

II. Further Process Steps for Producing the Catalyst (a) The homogenized mixture of metal salt and hydrotalcite (or the hydrotalcite-comprising starting material) is subjected to a low-temperature calcination. The low-temperature calcination is carried out by thermal treatment of the homogenized mixture in a temperature range from 100° C. to 500° C. for a time in the range from 0.1 h to 24 h. The material is preferably heated using a controlled heating rate. The heating rate is preferably less than 20° C./min, preferably less than 10° C./min and more preferably less than 5° C./min. The material obtained after the low-temperature calcination can be present as a finely divided powder or as coarsely particulate loose material. To be able to use the material as loose particulate catalyst, a shaping process can be necessary. As shaping step, it is possible to carry out, for example, comminution, milling, tableting or extrusion.

(b) The material which has been calcined at low temperature is preferably subjected to a shaping process in order to obtain a molded material. This shaping process can comprise one or more of the following steps:

b.i) compacting, b.ii) comminution, b.iii) sieving and/or b') tableting.

In a further process variant, the shaping process is an extrusion process. The melt-impregnated catalyst composition is, for example, processed by means of an extruder with additional additives to give the desired shaped bodies. When a shaping process by means of extrusion is used, it is conceivable that the process step of low-temperature calcination (iv) does not have to be carried out. The process can be carried out with the calcination occurring only after extrusion in the form of a high-temperature calcination step. In general, a precalcination is carried out before extrusion.

(c) The molded material always has to be subjected to a high-temperature calcination process. The target temperature in the high-temperature calcination is in the region of greater than or equal to 500° C., preferably in the range from 500 to 1000° C. The duration of the high-temperature calcination, i.e. the heating of the sample at the target temperature, is in the range from 0.1 to 24 h.

(d) The high-temperature calcination can be carried out in the presence of an oxygen-comprising atmosphere, preferably air. The heating of the sample to the target temperature is preferably carried out using a controlled heating rate, preferably a heating rate of less than 20°/min and more preferably less than 10° C./min.

In the production of the catalyst of the invention, it can be preferred for at least individual substeps of the production process to be carried out continuously. For example, particular preference is given to carrying out the low-temperature calcination in a continuously operated rotary tube furnace.

In a further process step, the calcined catalyst can be exposed to a reductive gas atmosphere while being heated in order to reduce at least part of the metal species, preferably of the nickel. This thermal treatment under a reductive gas atmosphere is preferably carried out in the same reactor in which the catalytic process is carried out.

In a particularly preferred embodiment, the invention provides a catalyst for the catalysis of heterogeneous reactions, preferably the reaction of methane, carbon dioxide and water to form synthesis gas, which comprises at least the three phases nickel-magnesium mixed oxide, magnesium spinel and aluminum oxide hydroxide and in which the nickel-magnesium mixed oxide has an average crystallite size of <100 nm, preferably <70 nm, more preferably <40 nm, and the magnesium spinel phase has an average crystallite size of <100 nm, preferably <70 nm, more preferably <40 nm, the proportion of nickel is in the range 7-28 mol %, that of magnesium is in the range 8-26 mol %, that of aluminum is in the range 50-70 mol % and the BET surface area is in the range 10-200 m$^2$/g.

Particular preference is also given to an embodiment of the catalyst of the invention which has a proportion of nickel in the range 6-30 mol % and a proportion of magnesium in the range from 8-38 mol %, preferably in the range 23-35 mol %. The proportion of aluminum is preferably in the range 50-70 mol %.

It should be emphasized that particularly high-performance catalysts and thus particularly preferred embodiments of the invention are obtained when the physicochemical properties of the catalysts have particular values.

In a preferred embodiment, the physicochemical properties selected from the group consisting of phase composition according to XRD, BET surface area, average pore diameter and/or tamped density of the catalyst of the invention have preferred values.

The phase composition of a particularly preferred catalyst is distinguished by the intensity of the diffraction reflection at 43.15°±0.15° 2θ (2 theta) (d=2.09±0.01 Å) being less than or equal to the intensity of the diffraction reflection at 44.83±0.20° 2θ (d=2.02±0.01 Å), with the intensity of the diffraction reflection at 43.15°±0.15° 2θ (2 theta) (d=2.09±0.01 Å) more preferably being less than the intensity of the reflection at 44.83±0.20° 2θ (d=2.02±0.01 Å) and the intensity ratio of the two diffraction reflections I(43.15°)/I (44.83°) even more preferably being from 0.3 to 1.0, preferably from 0.5 to 0.99, more preferably from 0.6 to 0.97 and particularly preferably from 0.7 to 0.92. A diffraction pattern (5-80° 2θ) of a catalyst according to the invention having a molar ratio of Ni/Mg/Al of 14/29/57 is depicted by way of example in figure I.

A particularly preferred embodiment of the catalyst has a BET surface area in the range from 10 to 200 m$^2$/g, preferably from 15 to 150 m$^2$/g, more preferably from 20 to 100 m$^2$/g, even preferably from 30 to 80 m$^2$/g, very particularly preferably from 30 to 78 m$^2$/g and in particular preferably from 30 to 78 m$^2$/g. The determination of the BET specific surface area was carried out in accordance with DIN 66131.

Furthermore, a preferred embodiment of the catalyst also has a characteristic tamped density which is preferably <1500 g/l, more preferably <1350 g/l and even more preferably ≤1100 g/l. The determination of the characteristic tamped density was carried out by means of an STAV 2003 tamped volumeter from JEL. A 0.5-1.0 mm fraction of crushed catalyst was used for the measurement.

III. Methanation Process

A further and important aspect of the invention relates to a methanation process, preferably high-temperature methanation, which has the features indicated in claims 7 to 14. The production of the catalyst according to the invention is carried out according to any of claims 1 to 4 or the methanation catalyst according to the invention can be produced according to either claim 5 or 6.

The methanation process of the invention can be carried out over a temperature range from 300° C. to 900° C. The methanation process of the invention is preferably carried out in a temperature range above 500° C., more preferably in a temperature range from 500° C. to 800° C., even more preferably in a temperature range from 600° C. to 750° C.

Here, the high thermal stability of the catalyst when carrying out the methanation process of the invention is particularly remarkable compared to when the process is carried out using a catalyst material known from the prior art. Owing to the high thermal stability of the catalyst of the invention, its deactivation is relatively low even under high thermal stress. The operating lives of the catalyst can be considerably lengthened by means of the process of the invention, which leads to an improvement in the economics of the process.

In addition to the improved thermal stability of the catalyst, the catalyst of the invention also has a higher mechanical hardness compared to comparable catalysts from the prior art. Owing to the increased mechanical stability, the process of the invention can be carried out at high process pressures. The process pressures can be in the range from 10 to 50 bar, usually from 20 to 30 bar, e.g. 25 bar.

The carbonization tendency in the process of the invention is low, which is necessary for maintenance of the high activity.

A preferred embodiment of the process of the invention relates to the methanation of synthesis gas having an $H_2/CO$ ratio in the range from 2.5 to 4, more preferably in the range from 3 to 3.5. In a particularly preferred embodiment of the process of the invention, the synthesis gas is provided, for example, from coal gasification (e.g. Lurgi process).

This synthesis gas originating from coal gasification is usually firstly purified before the methanation. For example, the sulfur-comprising components and a large part of the $CO_2$ are removed before carrying out the methanation.

It is a characteristic of the Lurgi process that a relatively high proportion of methane is present in the synthesis gas. After purification, the dry synthesis gas comprises the following main components in the following, typical concentrations in proportions by volume: ~35% by volume of $CH_4$, ~45% by volume of $H_2$ and ~15% by volume of CO; secondary components can be: $CO_2$ in particular, and also nitrogen or higher hydrocarbons, for example ethane. The reactor outlet temperature in the process is limited by the fact that the CO content in the synthesis gas is reduced by recirculation of part of the product stream in order to limit the heat evolved in the overall reaction.

When the synthesis gas originates from the Lurgi process, the catalyst is accordingly supplied with a synthesis gas having the following composition: $CH_4$ content in the range from 36 to 42% by volume, $H_2$ content in the range from 35 to 45% by volume, CO content in the range from 9 to 12% by volume, $H_2O$ content in the range from 8 to 12% by volume and $CO_2$ content in the range from 0 to 3% by volume.

Owing to the high thermal stability of the catalyst of the invention, the recycle stream can be dispensed with in a further embodiment and the purified synthesis gas from coal gasification, which has previously been subjected to the usual purification steps, can be used directly.

The synthesis gas can also comprise further components, for example nitrogen, argon, which themselves do not participate in the methanation reaction. The sulfur content of the synthesis gas should be as low as possible in order to avoid poisoning of the nickel sites by sulfidation.

The process of the invention makes it possible to achieve a high methane yield per nickel atom present on the catalyst support or comprised therein. It can be assumed that this is associated with the special structure of the catalyst material and the good accessibility of the active sites.

The mode of operation of the process of the invention is such that the GHSV thereof is in a range from 500 to 50 000 $h^{-1}$, preferably in a range from 1000 to 15 000 $h^{-1}$ and especially preferably in a range from 1000 to 5000 $h^{-1}$.

The use of the catalyst of the invention in the form of shaped bodies is also particularly advantageous for carrying out methanation reactions since it is possible to achieve a lower pressure drop within the reactor when using the shaped bodies than when using a catalyst in the form of a bed of unshaped material. The catalyst material is particularly suitable when employed in methanation reactions because of the high mechanical stability of the material.

With regard to shaped bodies, it may be said that these have a virtually identical shape and a particular minimum dimension in any direction of the three axes in space, with the dimension in each direction of an axis in space being greater than 2 mm.

EXAMPLES

Production Process

The process of the invention for producing the catalyst is illustrated by example M1. Firstly, 411.4 g of pulverulent nickel nitrate hexahydrate which had previously been crushed to a fine powder by means of a mortar and pestle and 600 g of hydrotalcite (Pural MG30 from Sasol) were intimately mixed to produce a premix of metal salt and hydrotalcite and introduced into the rotary tube of a rotary tube furnace. The premix was heated to 80° C. in the rotary tube furnace and maintained there at 80° C. for 1 hour, with the rotary tube and the premix present therein being rotated at two revolutions per minute and an air stream of 150 l/h being passed through the rotary tube. The weight of the premix obtained after cooling was 886 g.

400 g of the sample obtained during premixing were subsequently subjected to a low-temperature calcination. For this purpose, the sample was introduced into a fused silica flask, this was fastened in a rotary bulb furnace and heated therein at a heating rate of 5° C./min to a target temperature of 425° C. and heated at 425° C. for one hour. During the thermal treatment of the sample, the fused silica flask was rotated at a rotary speed of 12 revolutions per minute, with air simultaneously being passed through the flask at a flow rate of 1 l/min.

The sample obtained in the low-temperature calcination was mixed with graphite powder and pressed by means of a punch press to produce pellets. The graphite powder serves as lubricant and it is also possible to use stearic acid or magnesium stearate instead of graphite. The pellets produced by means of the press used here had a diameter of 4.75 mm and a thickness of about 4-5 mm. The lateral compressive strength of the pellets was 60-70 N.

The pellets were comminuted by means of a screen mill and pressed through a sieve in order to obtain a size fraction of <1.6 mm. The precompacted material was tableted again to give pellets having a diameter of 4.75 mm and a thickness of 3-4 mm. The pellets had a lateral compressive strength of 130-150 N.

The sample material obtained in this way was calcined at 850° C. for one hour in a muffle furnace through which air was passed and subsequently cooled to room temperature. The sample material placed in the muffle furnace was heated at a heating rate of 5° C./min from room temperature to 850° C. The air which was passed through the furnace during the heating-up phase, the calcination and the cooling phase had a flow rate of 6 l/min.

The calcined sample material was subjected to chemical and physical characterization. In the elemental analysis, the following composition was found: 21% by weight of NiO, 53% by weight of $Al_2O_3$ and 23% by weight of MgO, with the figures being based on the oxides. In the XRD analysis, magnesium spinel ($MgAl_2O_4$) and $MgNiO_2$ were detected as phases. The average crystallite size of the phases could be determined from the reflections using the Scherrer equation. The result was that the spinel particles had a crystallite size of 9.0 nm and the mixed oxide particles had a crystallite size of 16.5 nm.

The sample material was characterized by nitrogen sorption and Hg porosimetry. The sample material had a BET surface area of 67 $m^2/g$. The sample material had an Hg pore volume of 0.31 ml/g and a pore surface area of 83 $m^2/g$, with the sample material having a monomodal pore structure. The pores of the sample material had an average pore diameter of about 15 nm.

A further catalyst M2 was produced in a manner analogous to M1 but was calcined at a temperature of 950° C. The following composition was found by elemental analysis: 21% by weight of NiO, 53% by weight of $Al_2O_3$ and 23% by weight of MgO, where the figures are based on the oxides. In the XRD analysis, magnesium spinel ($MgAl_2O_4$) and $MgNiO_2$ were detected as phases (see figure I). From the reflections, the average crystallite size of the phases was determined more precisely using the Scherrer equation. The result was that the spinel particles had a crystallite size of 14 nm and the mixed oxide particles had a crystallite size of 13 nm.

The sample material was characterized by means of nitrogen sorption and Hg porosimetry. The sample material had a BET surface area of 58 $m^2$/g. The sample material had an Hg pore volume of 0.41 ml/g and a pore surface area of 48 $m^2$/g, with the sample material having a monomodal pore structure. The pores of the sample material had an average pore diameter of about 34 nm.

COMPARATIVE EXAMPLE

As comparative example CM1, the catalytic properties of a catalyst which had been produced by means of a precipitation process were tested. To produce this catalyst, 175.7 g of hydrotalcite (Pural MG30 from Sasol having a loss on ignition of 34.2% by weight) were firstly placed in a vessel comprising 6 l of deionized water which had been preheated to 48° C. In a separate vessel, a solution of nickel nitrate and aluminum nitrate was produced by dissolving 612.8 g of nickel nitrate hexahydrate and 313.1 g of aluminum nitrate nonahydrate in 509.2 g of deionized water and the solution was heated to 48° C. An aqueous sodium carbonate solution which had a sodium carbonate content of 20% by weight and had likewise been preheated to 48° C. was used as precipitation reagent.

To precipitate the metal species, the solution of the metal nitrate salts and the sodium carbonate solution were simultaneously introduced dropwise into the vessel comprising the aqueous hydrotalcite dispersion. The initial charge of the aqueous hydrotalcite dispersion was heated to 48° C. and the dispersion was mixed by means of a stirrer. During the addition of the salt solution and the precipitation reagent to the aqueous initial charge, the pH of the aqueous dispersion was monitored and the addition of the sodium carbonate solution was controlled so that the pH in the initial charge was maintained at a value of 8.0. After all the metal salt solution had been transferred to the vessel with the initial charge, a total of 3.5 l of sodium carbonate solution had been used as precipitation reagent.

After the precipitation was complete, the suspension obtained by the precipitation process was stirred for another 15 minutes and the precipitated product was subsequently filtered off by means of a suction filter. The filter cake was washed with deionized water, with the nitrate content of the filtrate being simultaneously determined. The temperature of the water used for washing was 20° C. The washing procedure was stopped as soon as nitrate ions could no longer be detected in the filtrate (the nitrate content was thus below the detection limit of 10 ppm). 350 l of water were required for washing the filter cake. The washed filter cake was subsequently dried at 120° C. in a drying oven for a period of 16 h.

The dried solid was heated at 700° C. in a muffle furnace for 5 h. The muffle furnace and the solid comprised therein were heated to 700° C. at a controlled heating rate and an air stream having a volume flow of 20 l/min was passed through the muffle furnace during heating. The solid obtained in this calcination was mixed with 3% by weight of graphite powder and the mixture was pressed by means of a punch press to produce pellets. The pellets obtained here had a diameter of 4.75 mm and a thickness of about 2 mm. The pellets were comminuted by means of a screen mill and pressed through a sieve having mesh opening of 1 mm in order to obtain a size fraction comprising particles smaller than 1 mm.

The particle fraction obtained after precompacting was admixed with 10% by weight of Puralox (boehmite from Sasol) and 3% by weight of graphite, intimately mixed and subjected to tableting. The pellets obtained here had a diameter of 4.75 mm and a thickness of about 3-4 mm. The lateral compressive strength of the pellets was 100 N.

The composition of the pellets or the calcined samples was determined by means of chemical analysis which showed that the material had an Ni content of 29.8% by weight, an Al content of 21.1% by weight, an Mg content of 4.7% by weight and a carbon content of 3.1% by weight. At a temperature of 900° C., the samples displayed a loss on ignition of 7.3% by weight. Based on the oxides, the following composition was determined for the calcined precipitation product: 41% by weight of NiO, 43% by weight of $Al_2O_3$, 8.4% by weight of MgO and 3.3% by weight of C.

In the XRD analysis of the calcined sample, nickel oxide (NiO) and nickel spinel ($NiAl_2O_4$) were identified. The nickel oxide particles had an average crystallite size of 5.0 nm determined by analysis of the corresponding reflections using the Scherrer equation.

The sample material had a BET surface area of 165 $m^2$/g. The sorption study was carried out using nitrogen. In analysis of the pore material by Hg porosimetry, a pore volume of 0.33 ml/g was found. The sample material displayed a bimodal pore structure: the major part of the pores had an average pore diameter of 6 nm and the smaller part of the pores had an average pore diameter of 30 nm. An average pore diameter of 11 nm was determined. Calculation of the surface area of the sample material on the basis of Hg analysis gave a surface area of 123 $m^2$/g.

Catalyst Testing

The catalysts of example M1, example M2 and comparative example CM1 were subjected to the process conditions of CO methanation in succession in an experimental reactor to produce synthetic natural gas in order to characterize the performance properties of the catalysts in respect of CO methanation. The experimental reactor was equipped with a reaction tube which before the individual tests had been charged with 50 ml of the respective catalyst sample (i.e. example M1, example M2 or comparative example CM1). In the charge, the catalyst samples were present in the form of pellets.

The catalyst of comparative example CM1 installed in the tube reactor and the test set-up was firstly subjected to activation. For this purpose, the catalyst CM1 was heated to 280° C. in the presence of a nitrogen stream and subsequently exposed to a reductive atmosphere for 16 hours by mixing 5% by volume of $H_2$ into the nitrogen stream. The catalysts according to the invention, example M1 and example M2, were not activated but instead installed and started up directly in the oxidic form. An advantage which may be mentioned is that it is possible to implement the process of the invention even without activating the catalysts.

After the activation under the reducing atmosphere in the case of CM1 or directly after installation in the case of M1 or M2, the methanation reaction was started, with the catalyst being exposed to a feed gas stream which had been pretreated to 280° C. The feed gas stream had a volume flow of 1202 standard l/h and comprised the six components hydrogen, CO, $CO_2$, $CH_4$, $N_2$ and $H_2O$ in the following ratio of the respective individual volume flows: 468 standard l/h of hydrogen, 132 standard l/h of CO, 12 standard l/h of $CO_2$, 456 standard l/h of $CH_4$, 24 standard l/h of $N_2$ and 110 standard l/h of $H_2O$. The experimental parameters chosen here and the plant configuration led to a reaction temperature in the range from 600 to 620° C. being established in the reactor while carrying out the methanation.

The feed gas stream and the product gas stream were each characterized in the water-free state by GC analysis. The characterization of the feed gas stream was carried out before the addition of water and the characterization of the product gas stream was carried out after the water had been condensed out. Tables 1 and 2.A give a summary of the measured data for the gas compositions of the feed and product streams. The respective values represent the average values determined from the individual values during the total time of the experiment.

The catalyst according to the invention (example M1) displayed a CO conversion of 93% and the comparative example (CM1) displayed a CO conversion of 88%. The CO conversion of example M1 was thus 5% above the conversion achieved using comparative example CM1. In addition, the catalyst according to the invention (example M1) could give the high conversion over a period of more than 1200 h, while the catalyst from comparative example CM1 displayed a significant decrease in activity after only about 300 h, leading to termination of the experiment. It is also noteworthy that the catalyst from example M1 not only displayed a higher activity and long-term stability but also had a significantly higher mechanical strength than the catalyst from comparative example CM1.

The catalysts of example M1, example M2 and comparative example CM1 were removed from the reaction tube after the methanation study had been carried out and subjected to characterization. The samples were the used catalyst from example M1, the used catalyst from example M2 and the used catalyst from comparative example CM1.

The catalyst according to the invention (example M2) displayed a higher CO conversion of 95%. The CO conversion achieved over the catalyst from example M2 was thus 2% above the conversion achieved using the catalyst from example M1. In addition, the catalyst according to the invention (example M2) was able to give a high conversion over a period of more than 480 h, while the catalyst from comparative example CM1 displayed a significant decrease in activity even after about 300 h, leading to the experiment being stopped. In addition, the catalyst from example M2 had a lateral compressive strength of 168 N and thus a greater mechanical strength than the catalyst from example M1.

Table 1 shows the composition of the feed gas before it was brought into contact with the catalyst and of the product gas obtained after contacting with the inventive catalyst example M1. The figures for the individual components are in % by volume. The duration of the catalysis experiment was 1200 h.

|        | Feed gas | Product gas |
|--------|----------|-------------|
| $CH_4$ | 37.1     | 53.0        |
| $H_2$  | 41.0     | 22.8        |
| CO     | 9.7      | 0.7         |
| $CO_2$ | 1.1      | 3.0         |
| $H_2O$ | 9.1      | 18.2        |
| $N_2$  | 2.0      | 2.3         |

Table 2.A shows the feed gas and product gas composition in the methanation test of the comparative catalyst (comparative example CM1) over a period of 300 h. After this time, a decrease in the conversion was observed, i.e. $H_2$ and CO content in the product stream increased and the $CH_4$ content decreased greatly. The figures for the individual components are given in % by volume.

|        | Feed gas | Product gas |
|--------|----------|-------------|
| $CH_4$ | 37.7     | 53.3        |
| $H_2$  | 40.5     | 22.2        |
| CO     | 9.6      | 1.2         |
| $CO_2$ | 1.1      | 2.6         |
| $H_2O$ | 9.1      | 18.4        |
| $N_2$  | 2.0      | 2.3         |

Table 2.B shows the composition of the feed gas before it was brought into contact with the catalyst and of the product gas obtained after contacting with the catalyst according to the invention from example M2. The figures for the individual components are % by volume. The duration of the catalysis experiment was 480 h.

|        | Feed gas | Product gas |
|--------|----------|-------------|
| $CH_4$ | 37.9     | 55.1        |
| $H_2$  | 41.7     | 21.2        |
| CO     | 9.9      | 0.5         |
| $CO_2$ | 1.1      | 2.4         |
| $H_2O$ | 8.5      | 18.2        |
| $N_2$  | 1.9      | 2.6         |

Table 3 shows the parameters determined by analysis of used catalyst from example 1 (after testing for 1200 h) and used catalyst CM1 (after testing for 300 h) by means of XRD, nitrogen sorption and Hg porosimetry. The Scherrer equation was used for estimating the crystallite size.

|     |           |                       | U example M1 | U comparative example CM1 |
|-----|-----------|-----------------------|--------------|---------------------------|
| XRD | $MgAl_2O_4$ | Content [mol %]     | 82           | /                         |
|     | $MgAl_2O_4$ | Crystallite size [nm] | 24.5      | /                         |
|     | $NiMgO_2$ | Content [mol %]       | 10           | /                         |
|     | $NiMgO_2$ | Crystallite size [nm] | 28.5        | /                         |
|     | Ni metal  | Content [mol %]       | 8            | /                         |
|     | Ni metal  | Crystallite size [nm] | 54.5         | 40.5                      |

-continued

|  |  |  | U example M1 | U comparative example CM1 |
|---|---|---|---|---|
| BET surface area | using Na | [m²/g] | 19 | 39 |
| Hg porosimetry |  | [g/ml] | 0.31 | 0.41 |
| Pore structure |  |  | monomodal | bimodal |
|  | average pore diameter | [nm] | 58-60 | 60, 30 |
| Pore surface area | Hg measurement | [m²/g] | 21 | 41 |
| Lateral compressive strength |  | [N] | 85 | 12 |

Physical Characterization

The XRD analyses were carried out by means of a D8 Advance Series 2 from Bruker/AXS using a CuK-alpha source (having a wavelength of 0.154 nm at 40 kV and 40 mA). The measurements were carried out over the measurement range 5-80° (2-theta) in 0.02° steps at 4.8 seconds/step. The structure analysis software TOPAS (Bruker AXS) was used to determine the average crystallite sizes of the individual phases.

FIG. 1 shows a representation of the powder diffraction pattern which was taken on the catalyst sample example M2 after the high-temperature calcination.

The invention claimed is:

1. A process for producing a methanation catalyst, the process comprising:
   (i) contacting a fusible metal salt and a finely divided hydrotalcite-comprising starting material,
   (ii) intimately mixing by mechanical mixing the fusible metal salt and the hydrotalcite-comprising starting material, thereby obtaining a mixture of the fusible metal salt and the hydrotalcite-comprising starting material,
   (iii) thermally treating said mixture of said fusible metal salt and said hydrotalcite-comprising starting material under a condition wherein the fusible metal salt is present in a form of a metal salt melt, optionally at a temperature of from 30 to 250° C.,
   (iv) calcining a thermally treated mixture at a temperature of <500° C., optionally for a duration of from 0.1 to 24 hours,
   (v) molding or shaping a product of calcining said thermally treated mixture, and
   (vi) further calcining a molded or shaped product of calcining said thermally treated mixture at a temperature of ≥500° C., optionally for a duration of from 0.1 to 24 hours thereby obtaining the methanation catalyst.

2. The process according to claim 1, wherein said calcining (iv) and said calcining (vi) are carried out at a heating/cooling rate of from 0.01 to 10° C. per minute, and
   optionally said mixing (ii) is carried out simultaneously with said thermally treating (iii).

3. The process according to claim 1, wherein said thermally treating (iii) is carried out directly before said calcining (iv).

4. The process according to claim 1, wherein the fusible metal salt comprises a nickel salt, a cobalt salt, or both, optionally in a form of a hexahydrate.

5. A catalyst for carrying out a methanation reaction, wherein the catalyst is obtained by the process according to claim 1.

6. The catalyst according to claim 5, wherein said calcining (iv) and said calcining (vi) are carried out in the presence of an oxygen-comprising atmosphere optionally at a heating rate of less than or equal to 20° C/min.

7. A process for carrying out a methanation reaction, the process comprising:
   introducing the catalyst according to claim 5 into the methanation reaction, and
   carrying out the methanation reaction at a temperature of from 300° C. to 900° C. and a pressure of from 10 to 50 bar.

8. A methanation process, comprising:
   a.1) treating a catalyst precursor material in a reducing gas atmosphere before carrying out the methanation,
   a.2) heating a feed fluid stream comprising a synthesis gas comprising CO, $CO_2$, or both, and
   a.3) subsequently contacting the synthesis gas with the catalyst according to claim 5.

9. The methanation process according to claim 8, wherein said contacting a.3) occurs at a temperature of from 300° C. to 900° C.

10. The methanation process according to claim 8, wherein the synthesis gas has an $H_2$/CO ratio of from 2.5 to 4.

11. The methanation process according to claim 8, wherein the synthesis gas has a $CH_4$ content of greater than or equal to 10% by volume.

12. The methanation process according to claim 8, wherein the synthesis gas has a water vapor content of from 2 to 16% by volume.

13. The methanation process according to claim 8, wherein the synthesis gas comprises:
   $CH_4$ of from 36 to 42% by volume,
   $H_2$ of from 35 to 45% by volume,
   CO of from 9 to 12% by volume,
   $H_2O$ of from 8 to 12% by volume, and
   $CO_2$ of from 0 to 3% by volume.

14. The methanation process according to claim 8, wherein a product stream having a CO content of ≤2% by volume is obtained and optionally at least part of the product stream is fed back into the feed fluid stream and contacted with the catalyst again.

* * * * *